(12) United States Patent
Amano

(10) Patent No.: US 6,506,198 B1
(45) Date of Patent: Jan. 14, 2003

(54) CORNEAL SURGICAL APPARATUS

(75) Inventor: Masanori Amano, Aichi (JP)

(73) Assignee: Nidek Co., Ltd., Aichi (JP)

( * ) Notice: Subject to any disclaimer, the term of this patent is extended or adjusted under 35 U.S.C. 154(b) by 298 days.

(21) Appl. No.: 09/676,661

(22) Filed: Oct. 2, 2000

(30) Foreign Application Priority Data

Sep. 30, 1999 (JP) .......................................... 11-280373

(51) Int. Cl.⁷ ................................................ A61F 9/00
(52) U.S. Cl. ..................................................... 606/166
(58) Field of Search ............................... 606/166, 169, 606/167, 107

(56) References Cited

U.S. PATENT DOCUMENTS

| | | | | |
|---|---|---|---|---|
| 2,480,737 A | * | 8/1949 | Jayle | 606/166 |
| 4,173,980 A | * | 11/1979 | Curtin | 606/107 |
| 4,423,728 A | * | 1/1984 | Lieberman | 606/166 |
| 4,660,556 A | * | 4/1987 | Swinger et al. | 606/166 |
| 4,662,370 A | | 5/1987 | Hoffmann et al. | 606/166 |
| 4,903,695 A | | 2/1990 | Warner et al. | 606/4 |
| 4,943,296 A | * | 7/1990 | Funakubo et al. | 606/166 |
| 5,133,726 A | | 7/1992 | Ruiz et al. | 606/166 |
| RE35,421 E | | 1/1997 | Ruiz et al. | 606/166 |
| 5,595,570 A | | 1/1997 | Smith | 606/166 |
| 5,624,456 A | | 4/1997 | Hellenkamp | 606/166 |
| 5,779,723 A | | 7/1998 | Shwind | 606/166 |
| 5,944,731 A | * | 8/1999 | Hanna | 606/166 |
| 5,980,543 A | | 11/1999 | Carriazo et al. | 606/166 |
| 6,059,805 A | * | 5/2000 | Sugimura et al. | 606/166 |
| 2001/0004702 A1 | * | 6/2001 | Peyman | 606/166 |

FOREIGN PATENT DOCUMENTS

| | | | |
|---|---|---|---|
| EP | 0 956 840 A2 | 11/1999 | A61F/9/00 |
| EP | 1 033 120 A2 | 9/2000 | A61F/9/013 |

* cited by examiner

*Primary Examiner*—Rodney M. Lindsey
(74) *Attorney, Agent, or Firm*—Sughrue Mion, PLLC

(57) ABSTRACT

A corneal surgical apparatus for incising a cornea of a patient's eye in a layered form has a suction ring having an opening, which is vacuum-fixed to the patient's eye so that the cornea is projected from the opening. A cutting unit has a blade and an applanating member so that the cornea projected from the opening is incised by the blade while being applanated by the applanating member. A height changing mechanism is further provided, for changing a height of a tip of the blade in a visual axis direction of the patient's eye with respect to the suction ring.

10 Claims, 8 Drawing Sheets

CORNEAL SURGICAL APPARATUS

BACKGROUND OF THE INVENTION

1. Field of the Invention

The present invention relates to a corneal surgical apparatus for incising the cornea of an eye of a patient in a layered format the time of a keratorefractive surgery or the like.

2. Description of the Related Art

In recent years, attention has been focused on LASIK (laser in situ keratomileusis) surgery for effecting keratorefractive treatment wherein after a flap is formed by incising a corneal portion with a thickness of 150 μm ranging from the corneal epithelium to the corneal stroma with one end of the cornea remaining connected like a hinge, the corneal stroma is cut away or ablated in a refractive correction amount by excimer laser light, and the flap is then returned to its original position. In this LASIK surgery, a corneal surgical apparatus called a microkeratome is used to incise the cornea in a layered form.

A typical microkeratome includes a suction ring having an opening, which is to be vacuum-fixed to a part of the cornea ranging from a corneal ring portion to the surface of the conjunctiva, a cornea applanating member for flatly applanating the cornea projected from the opening, and a blade moved in the direction toward the hinge while being oscillated in the lateral direction so as to incise the flattened cornea into a layered form with a substantially uniform thickness.

Since the corneal curvature of the patient's eye differs depending on individuals, a height of the cornea projected from the opening of the suction ring vacuum-fixed differs, and thus the diameter of the flap formed as a consequence of the corneal incision also differs. That is, as the height of the projected cornea is larger, the diameter of the formed flap is larger. For this reason, plural kinds of suction rings having respective, different opening diameters must be preliminarily prepared, so that an appropriate one of the suction rings is selected depending on the corneal curvature of the patient's eye to make the height of the projected cornea uniform and to form the flap having the uniform diameter. Alternatively, such a device has been proposed that, as shown in FIGS. 11(a) and 11(b), the height of the suction ring (an outer suction ring) can be adjusted to make the height of the cornea projecting from the opening uniform, thereby forming the flap having the uniform diameter.

The above-noted procedures can be used in a case where the diameter of a flap is changed. That is, if the diameter of the flap should be made large or small, an appropriate one is selected from plural suction rings having respective, different opening diameters or the height of the suction ring is adjusted, thereby changing the height of the cornea projected from the opening.

The provision of the plural kinds of the suction rings increases the cost, and the interchange of the suction rings depending on the patient's eye requires troublesome work. The height adjustment of the suction ring requires, particularly, an unskilled operator, to take time, resulting in an extra load on the patient.

SUMMARY OF THE INVENTION

In view of the above-described problems, it is an object of the present invention to provide a corneal surgical apparatus, which is simple in structure and which is capable of forming a flap having a uniform diameter regardless of the differences in corneal curvature.

Another object of the present invention is to provide a corneal surgical apparatus, which can easily change the flap diameter.

To achieve the above-noted objects, the present invention is characterized by the following features.

(1) A corneal surgical apparatus for incising a cornea of a patient's eye in a layered form, comprising:
 a suction ring having an opening, which is vacuum-fixed to the patient's eye so that the cornea is projected from the opening;
 incising means, having a blade and an applanating member, for incising the cornea projected from the opening using the blade while applanating the cornea using the applanating member; and
 height changing means for changing a height of a tip of the blade in a visual axis direction of the patient's eye with respect to the suction ring.

(2) The apparatus of (1), wherein the incising means includes a shaft for linearly moving the blade in an incise direction, and the height changing means includes tilting means for tilting the shaft in the visual axis direction.

(3) The apparatus of (2), wherein the tilting means includes a fulcrum member about which the shaft is inclined.

(4) The apparatus of (1), wherein the incising means includes a shaft for linearly moving the blade in an incise direction, and the height changing means includes moving means for translating the shaft parallelly in the visual axis direction.

(5) The apparatus of (4), wherein the moving means includes a guide member for guiding parallel translation of the shaft.

(6) The apparatus of (1), wherein the incise means includes a shaft for linearly moving the blade in an incise direction, first driving means for moving the shaft forwardly, second driving means for rotating the shaft, and transmitting means for converting rotation of the shaft into lateral oscillations and transmitting the lateral oscillations to the blade.

(7) The apparatus of (1), further comprising:
 informing means for providing information concerning the height of the tip of the blade in the visual axis direction, changed by the height changing means.

(8) A corneal surgical apparatus comprising:
 a main body;
 a suction ring fixedly provided on the main body, the suction ring having an opening;
 a cutting unit movable substantially along a plane of the opening;
 a drive unit supporting the cutting unit;
 a support movably supporting the drive unit to the main body, and holding, through the drive unit, the cutting unit at a variable position in a direction substantially perpendicular to the plane of the opening.

(9) The apparatus of (8), wherein the support includes a fulcrum member about which the drive unit is pivotable, and a threading member rotatably held by the main body and threadingly engaged with the drive unit.

(10) The apparatus of (8), wherein the support includes a guide rail movably supporting the drive unit, a rack member provided to the drive unit, and a pinion member rotatably held by the main body and meshed with the rack member.

The present disclosure relates to the subject matter contained in Japanese patent application No. Hei. 11-280373 (filed on Sep. 30, 1999), which is expressly incorporated herein by reference in their entireties.

DESCRIPTION OF THE PREFERRED EMBODIMENT

First Embodiment

Figure 1:
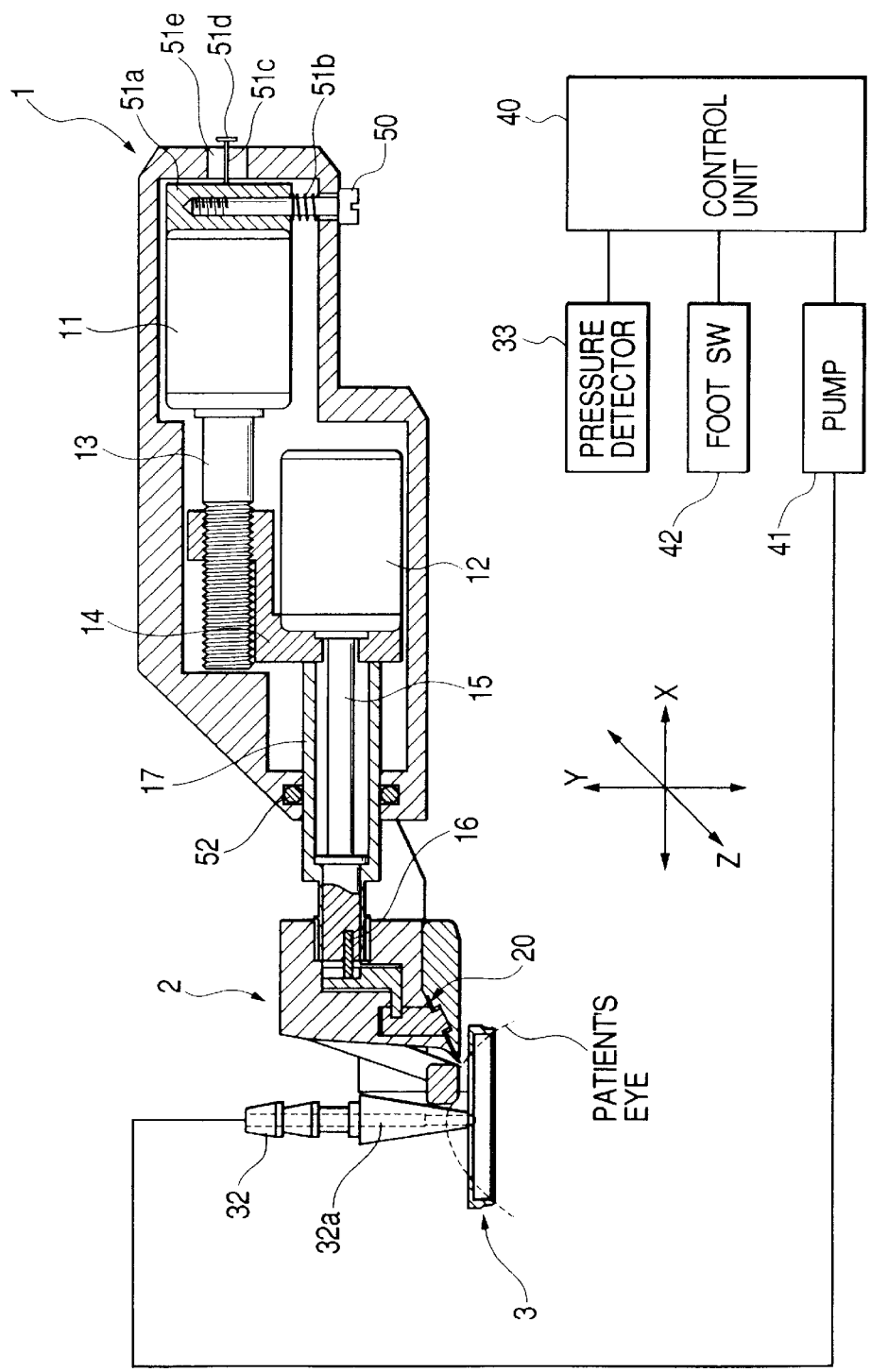
FIG. 1 is a cross-sectional view and a control system diagram of a corneal surgical apparatus in accordance with a first embodiment of the present invention.

Referring to the accompanying drawings, a description will be given of a first embodiment of the present invention. FIG. 1 is a cross-sectional view and a control system diagram of a corneal surgery apparatus in accordance with a first embodiment of the present invention.

Reference numeral 1 denotes a main body of the corneal surgery apparatus (microkeratome). A suction unit 3 for fixing the apparatus to the patient's eye and a cutting unit 2, which has a blade 20 (which will be described later) for incising the cornea and is adapted to move rectilinearly on the suction unit 3, are provided on the front side (left-hand side in the drawing) of the main body 1.

A feed motor 11 for rectilinearly moving the cutting unit 2 in the incising direction (in the X direction) and an oscillating motor 12 for imparting oscillations in the lateral direction (in the Z direction) to the blade 20 are installed in the main body 1. A feed screw 13 is coupled to a rotating shaft of the motor 11, which has a threaded portion corresponding in length to the rectilinear movement or travel of the cutting unit 2. An attaching member 14 is threadedly engaged with the screw 13. The motor 12 as well as a connecting member 17 for connecting the motor 12 and the cutting unit 2 are fixed to the attaching member 14. As the motor 11 is rotated forwardly or reversely, the motor 12 and the connecting member 17 move forwardly or backwardly (in the X direction) through the screw 13 and the attaching member 14, thereby causing the cutting unit 2 to move forwardly or backwardly. Further, a rotating shaft 15 is rotatably held by the connecting member 17. An eccentric shaft 16 is embedded on a distal end of the rotating shaft 15 at a position offset from the center of rotation, and the eccentric shaft 16 imparts lateral oscillations to the blade 20 (which will be described later).

Figure 5:
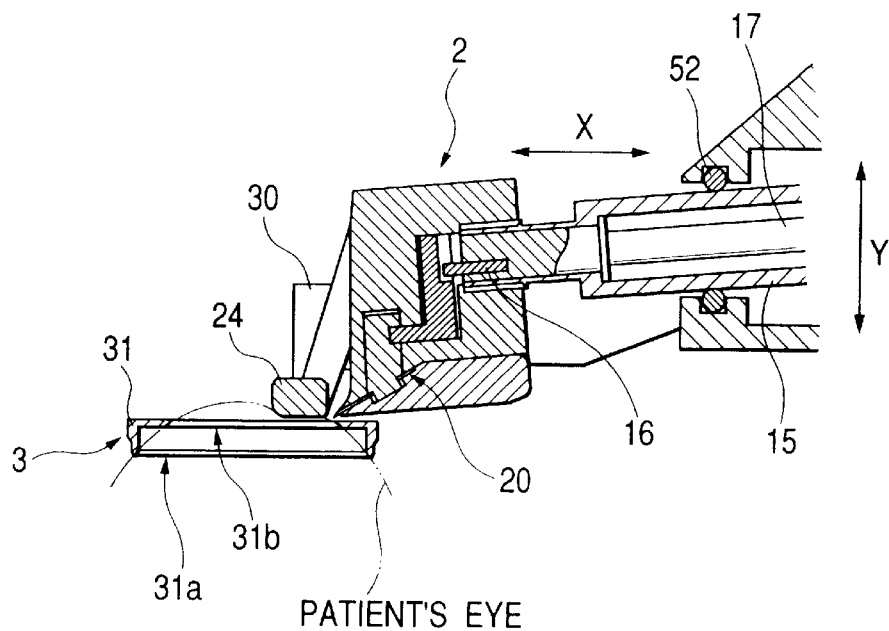
FIG. 5 is an explanatory diagram illustrating how the height of a blade relative to a suction ring is changed.
Figure 10A:
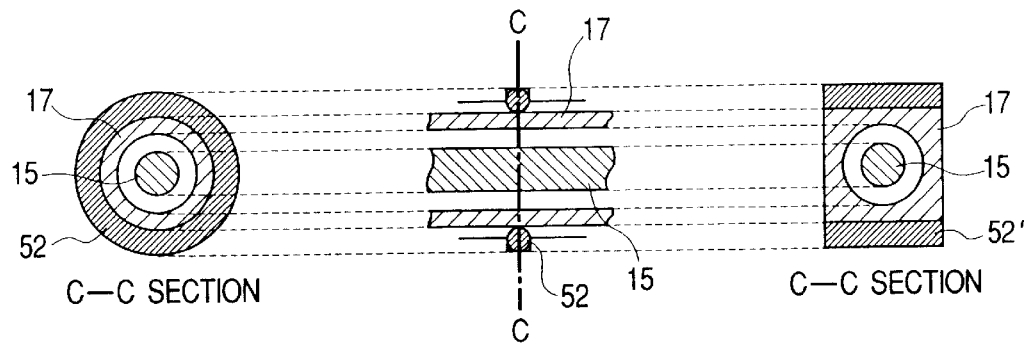
FIG. 10A, FIG. 10B and FIG. 10C are diagrams for explaining a fulcrum member and a shielding member.

The motor 11, the motor 12, the screw 13, the attaching member 14, and the connecting member 17 are tiltable vertically (in the Y direction) in a pivotable manner about a fulcrum member 52 provided on a front portion of the main body 1 (these members are immovable in the Z direction). FIG. 10A is a diagram for explaining the fulcrum member 52. A left part and a central part of FIG. 10A shows the fulcrum member 52 used in this embodiment, which is an O-ring-like member circumscribing the connection member 17 circular in outer configuration. As shown in a right part of FIG. 10A, in a case where the connecting member 17 is rectangular in outer configuration, it is preferable that a pair of columnar members 52' are respectively disposed on the upper and lower parts of the connecting member 17 to constitute the fulcrum member 52. Reference numeral 50 denotes a tilting screw which is inserted in a screw receiving portion 51a through a spring 51b from a bottom portion of the main body 1. The screw receiving portion 51a is attached to the motor 11, and the spring 51b is adapted to urge the spring receiving portion 51a in the upward direction. By virtue of this arrangement, as the screw 50 is rotated, the screw receiving portion 51a can be moved in the vertical direction (in the Y direction). Consequently, the motor 11, the motor 12, the screw 13, the attaching member 14, and the connecting member 17 are tilted vertically about the fulcrum member 52, thereby changing the height position of the cutting unit 2 attached to the front side of the connecting member 17 (that is, the height in the direction of the visual axis of the patient's eye can be varied), as shown in FIG. 5.

Reference numeral 51c denotes a shaft provided fixedly to the screw receiving portion 51a, and the shaft 51c is passed through a slot 51e provided in the rear portion of the main body 1 and has a scale member 51d at its tip. As the screw receiving member 51a is moved vertically by the rotation of the screw 50, the scale member 51d also moves vertically together with the shaft 51c.

Figure 2:
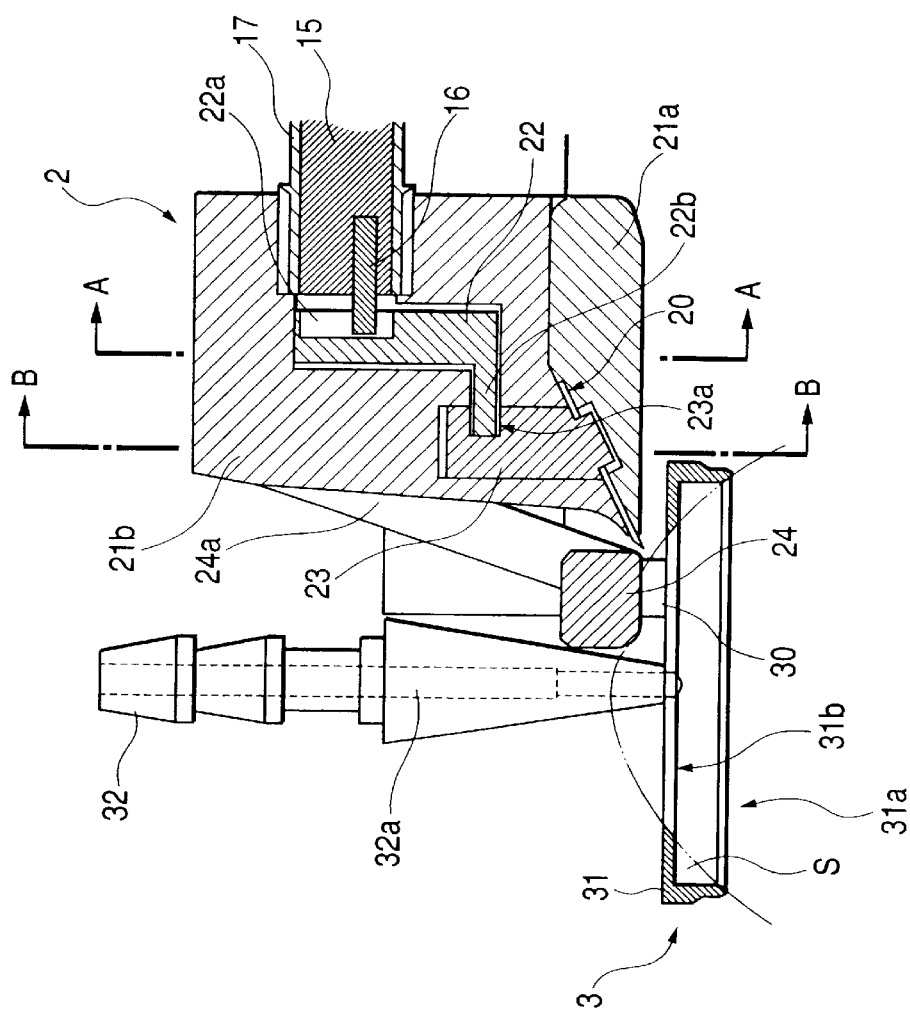
FIG. 2 is an enlarged explanatory diagram of a cutting unit and a suction unit of the apparatus.
Figure 3:
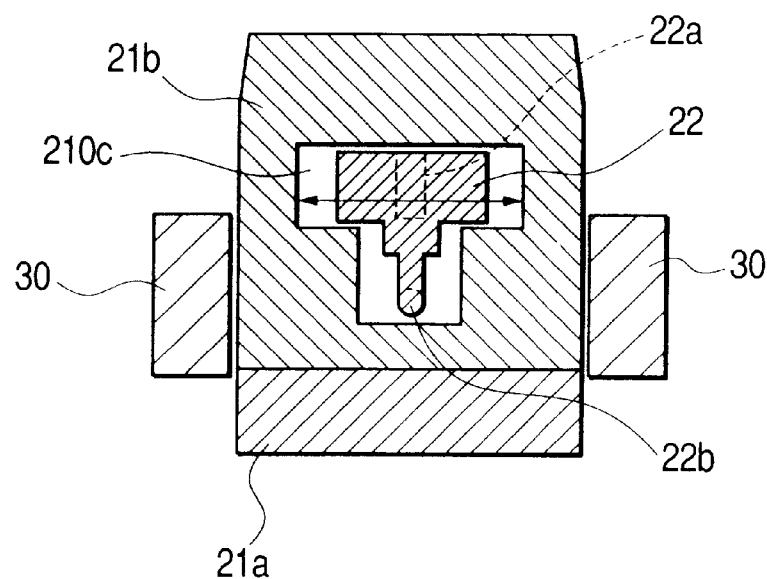
FIG. 3 is a cross-sectional view, taken along line A—A of FIG. 2, illustrating the cutting unit.
Figure 4:
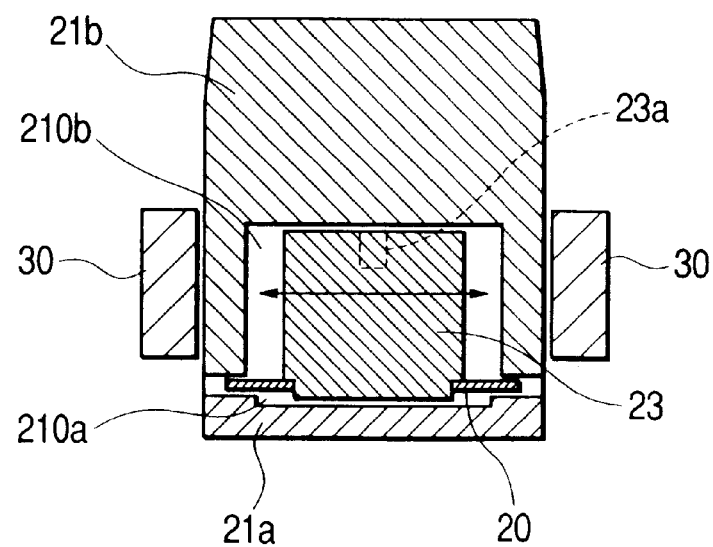
FIG. 4 is a cross-sectional view, taken along line B—B of FIG. 2, illustrating the cutting unit.

Referring next to FIGS. 2, 3 and 4, a description will be given of the arrangements of the cutting unit 2 and the suction unit 3. FIG. 2 is an enlarged view of the cutting unit 2 and the suction unit 3 shown in FIG. 1. FIG. 3 is a cross-sectional view taken along line A—A of FIG. 2. FIG. 4 is a cross-sectional view taken along line B—B of FIG. 2.

The cutting unit 2 is comprised of the blade 20 for corneal incision; a blade holder 21a and a holder block 21b for holding the blade 20 in such a manner as to permit lateral oscillations; a first oscillation transmitting member 22 for transmitting the lateral oscillations generated by the eccentric shaft 16; a second oscillation transmitting member 23 for transmitting the lateral oscillations by the first transmitting member to the blade 20, and a cornea applanating member 24 fixed to the block 21b by means of an attaching member 24a. A rotation hole into which the rotating shaft 15 is inserted is provided inside the block 21b, and a tip portion of the connecting member 17 is fixed thereto.

A metal blade having a blade edge of stainless steel, steel, or the like or a mineral blade having a blade edge of diamond, sapphire or the like is used as the blade 20. The blade 20 is held between the holder 21a and the block 21b at an appropriate angle with respect to the horizontal plane in such a manner as to be capable of undergoing lateral oscillations. On the holder 21a side, a shallow recess 210a is formed at a portion where the blade 20 is placed, and the lateral width of the recess 210a is set to be larger than the oscillating width for the lateral oscillations of the blade 20.

The first transmitting member 22 is movable in the lateral direction within a receiving groove 210c formed in the block 21b. The upper and lower portions of the first transmitting member 22 is held by the block 21b. A vertical groove 22a for engagement with the eccentric shaft 16 is formed in the first transmitting member 22. When the rotating shaft 15 is rotated by the rotative driving of the motor 12, the eccentric shaft 16 engaged with the vertical groove 22a applies a lateral driving force to the first transmitting member 22. This causes the first transmitting member 22 to oscillate laterally.

The second transmitting member 23 is movable in the lateral direction within the receiving groove 210b formed in the block 21b. The upper portion and the lower portion of the second transmitting member 23 are respectively held by the block 21b and the blade holder 21a. The first transmitting member 22 is provided at its lower-portion with a protrusion 22b projected to the blade 20 side, and the second transmitting member 23 is formed with a vertical groove 23a engaged with the protrusion 22b. As the first transmitting member 22 is oscillated laterally by the rotation of the rotating shaft 15 (circumferential motion of the eccentric shaft 16), the protrusion 22b engaged with the vertical groove 23a is laterally oscillated, thereby applying lateral kinematics force to the second transmitting member 23. Accordingly, the second transmitting member 23 is laterally oscillated together with the blade 20 fixed to the second transmitting member 23.

The cornea applanating member 24 is provided on the front side (left-hand side in FIG. 2) of the blade 20 so as to flatly applanate the cornea of the patient s eye in advance of the corneal incision by the blade 20 as the cutting unit 2 is moved forwardly. Since the blade 20 incises the cornea thus applanated flatly by the applanating member 24, a flap of a uniform layer is formed.

In this embodiment, the distance between the edge of the blade 20 attached to the holder 21a and the lower surface of the applanating member 24 is set to be about 150 microns ($\mu$m) so that the cornea can be incised with this thickness in a layered form.

The suction unit 3 includes a fixing member 30, a suction ring 31, and a suction pipe 32. The suction ring 31 is fixed to the main body 1 by the fixing member 30. The suction ring 31 has a substantially hollow cylindrical shape (a substantially U-shape in section), which has a circular recessed portion 31a adapted to abut against the patient's eye, and an opening 31b concentric to the recessed portion 31a. When the suction ring 31 is mounted on the patient's eye in place for surgery, the cornea of the patient's eye projects upward from the opening 31b, and a lower end portion of the suction ring 31 and an opening end portion (a periphery) of the opening 31b are caused to abut against the patient's eye to define a space S for suction.

The suction pipe 32 is embedded in the suction ring 31, and connected through an unillustrated vacuum tube to a pump 41. A suction passage 32a provided inside the suction pipe 32 communicates with the recessed portion 31a, and as the air inside the space S is sucked and discharged by the pump 41 through the passage 32a, the suction ring 31 is vacuum-fixed to the patient's eye. In this fixation, as the operator holds the main body 1, the positioning of the opening 31b can be facilitated, and the apparatus can be held stably.

In addition, an unillustrated pressure detection pipe is embedded on the suction ring 31, and the pressure detection pipe is connected to a pressure detector 33 through an unillustrated tube. The detector 33 detects, through the pressure detection pipe, the air pressure inside the space S sucked by the pump 41. A control unit 40 controls the operation of the motor 11, motor 12, the pump 41, etc. on the basis of the air pressure detected by the detector 33.

Hereafter, a description will be given of the operation of the apparatus having the above-described configuration. While confirming the state of inclination of the suction ring 31 (main body 1), the position of the pupillary center, and the like on the basis of a mark that has been preliminarily applied on the patient's cornea using an instrument such as a marker, the operator aligns the center of the opening 31b with the pupillary center, and disposes the suction ring 31 on the patient's eye.

After installation of the suction ring 31, the operator, while keeping the position and the posture of the main body 1, operates the pump 41 to suck the air in the space S between the suction ring 31 and the patient's eye to thereby decrease the air pressure (toward the negative pressure). When the air pressure in the space S is decreased to a fixed value (when it reaches a sufficient negative pressure), the operation of the pump 41 is controlled by a control unit 40 so as to maintain that air pressure. Accordingly, the suction ring 31 is vacuum-fixed onto the patient's eye.

Upon completion of the fixing of the apparatus, the cutting unit 2 is tilted using the screw 50 to adjust the height of the tip (blade edge) of the blade 20 with respect to the suction ring. 31. If the cutting unit 2 is inclined in an upwardly oriented manner, the height of the blade edge becomes large, and a small flap is formed as compared to a state in which the cutting unit 2 is horizontal. On the other hand, if the cutting unit 2 is inclined in a downwardly oriented manner, the height of the blade edge becomes small, and a large flap is formed as compared to the state in which the cutting unit 2 is horizontal. Accordingly, it suffices that in a case where the corneal curvature is large and thus the height of the cornea projecting from the suction ring 31 (the opening 31b) becomes large, the cutting unit 2 is inclined in the upwardly oriented manner, whereas in a case where the corneal curvature is small and thus the height of the cornea projecting from the suction ring 31 becomes small, the cutting unit 2 is inclined in the downwardly oriented manner. Similarly, it suffices that in a case where the flap diameter is to be small, the cutting unit 2 is inclined in the upwardly oriented manner, whereas if the flap diameter is to be large, the cutting unit 2 is inclined in the downwardly oriented manner. In the apparatus of this embodiment, if the height of the blade edge is changed by 0.1 mm in a case where the corneal curvature is 7.8 mm, the flap diameter is changed by 0.3 mm.

Figure 6:
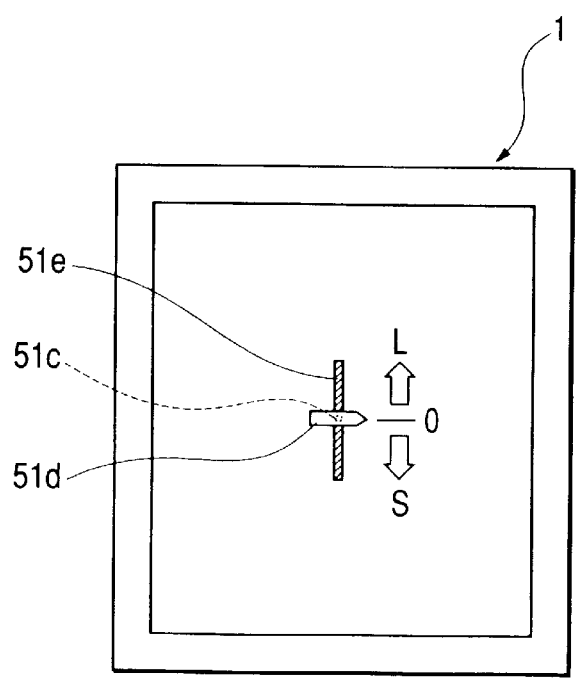
FIG. 6 is an explanatory diagram illustrating how the height of the blade relative to the suction ring is notified to an operator.

It should be noted that the state of inclination of the cutting unit 2 can be known from the amount of movement of the scale member 51d (see FIG. 6). When the scale member 51d is moved upward, the cutting unit 2 is inclined in the downwardly oriented manner, so that the flap is formed to be large. Meanwhile, when the scale member 51d is moved downward, the cutting unit 2 is inclined in the upwardly oriented manner, so that the flap is formed to be small. Further, if graduations for tilted positions which impart optimum flap diameters depending on the values of the corneal curvature are inscribed in advance, the use of the apparatus can be facilitated.

After completion of the height adjustment of the blade 20, the operator operates the foot switch 42 to rotatively drive the motor 11 and the motor 12. Upon reception of the drive instruction signal by the foot switch 42, the control unit 40 controls the rotational driving of the motor 12 so that the blade 20 is oscillated laterally at a fixedly set or variably set oscillating speed. The control unit 40 controls the rotational driving of the motor 11 so that the cutting unit 2 is rectilinearly moved toward the hinge (in the incise direction). Concurrently, the rotating shaft 15 slides in the advancing direction integrally with the cutting unit 2 while making rotational motion for imparting lateral oscillations to the blade 20.

When the flap formation is complete, that is, the edge of the blade 20 has incised the cornea with the hinge portion left, the motor 11 is rotated reversely to return the cutting unit 2 to its initial position. For this return operation, the rotation of the motor 12 is stopped using the independent control of the motors 11 and 12, to thereby withdraw or remove the blade 20 from the flap while avoiding the unnecessary oscillation of the blade 20. This reduces the possibility that the flap thus formed is cut off during the course of the return operation.

After the cutting unit 2 is returned to its initial position, the air is introduced into the space S to release the suction, and the apparatus (the suction ring 31) is removed. Subsequently, a refractive correction amount of the corneal stroma is ablated and removed using excimer laser light, and then the flap is returned to its original position, thereby completing the surgery.

Second Embodiment

Figure 7:
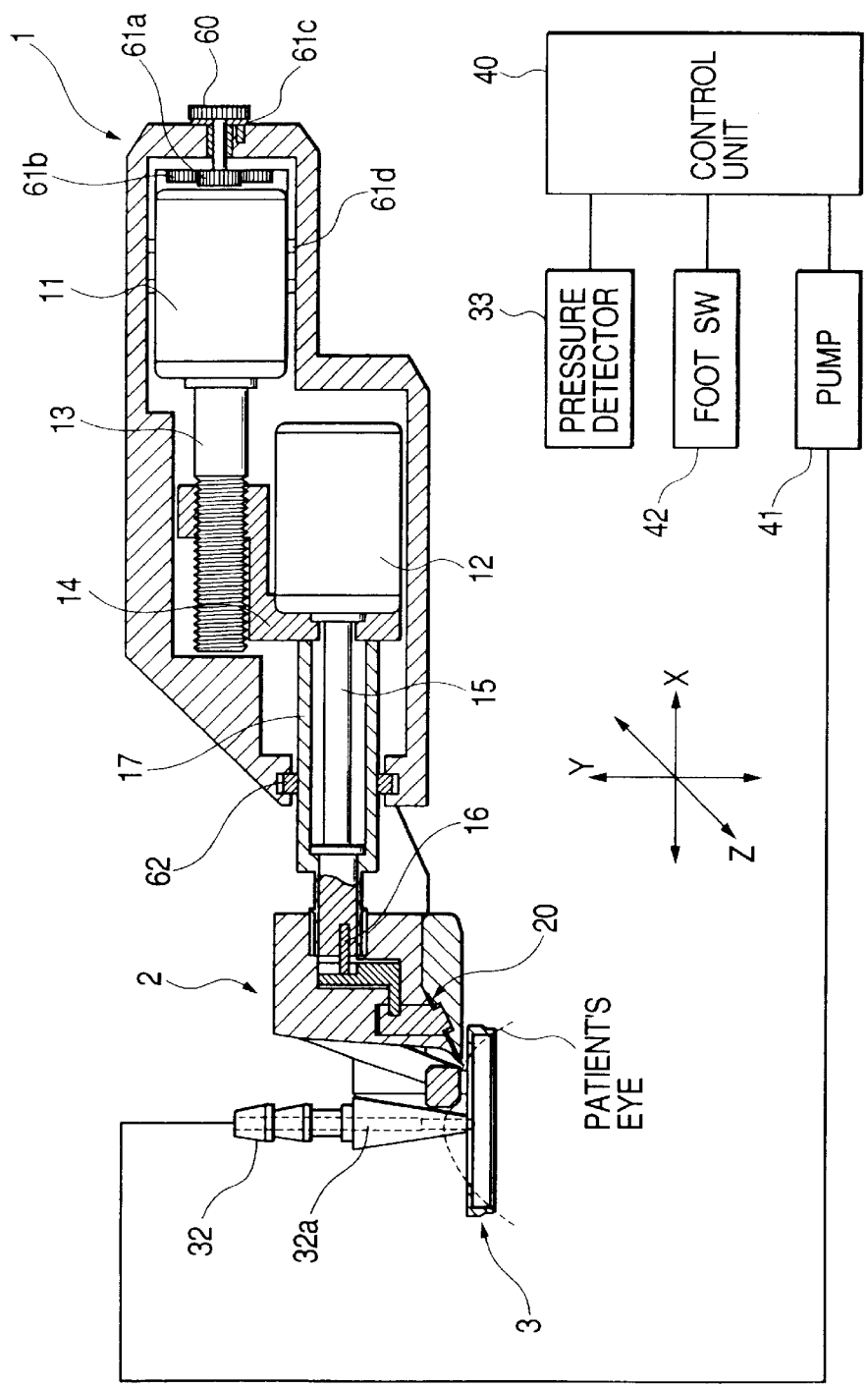
FIG. 7 is a cross-sectional view and a control system diagram of a corneal surgical apparatus in accordance with a second embodiment of the present invention.

FIG. 7 is a cross-sectional view and a control system diagram of a corneal surgical apparatus in accordance with a second embodiment of the invention. It should be noted that component parts that are identical to those of the first embodiment are denoted by the same reference numerals.

Figure 10B:
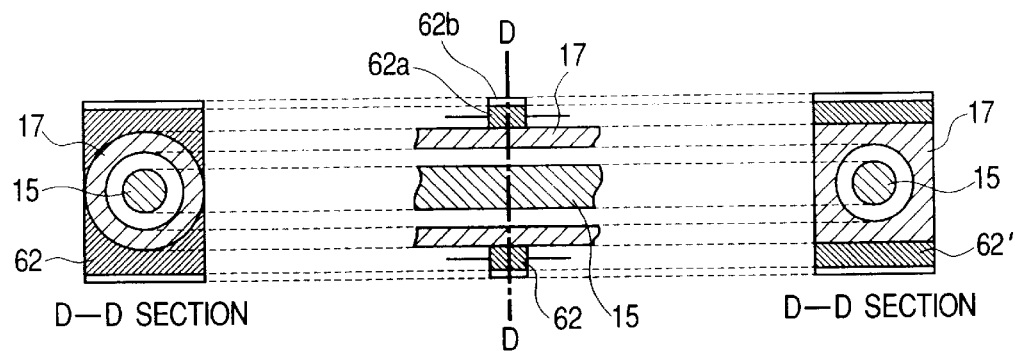
Figure 10C:
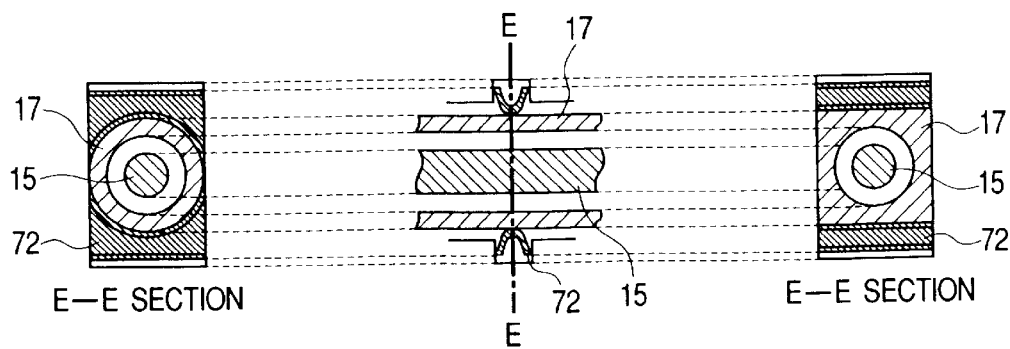
Figure 11A:
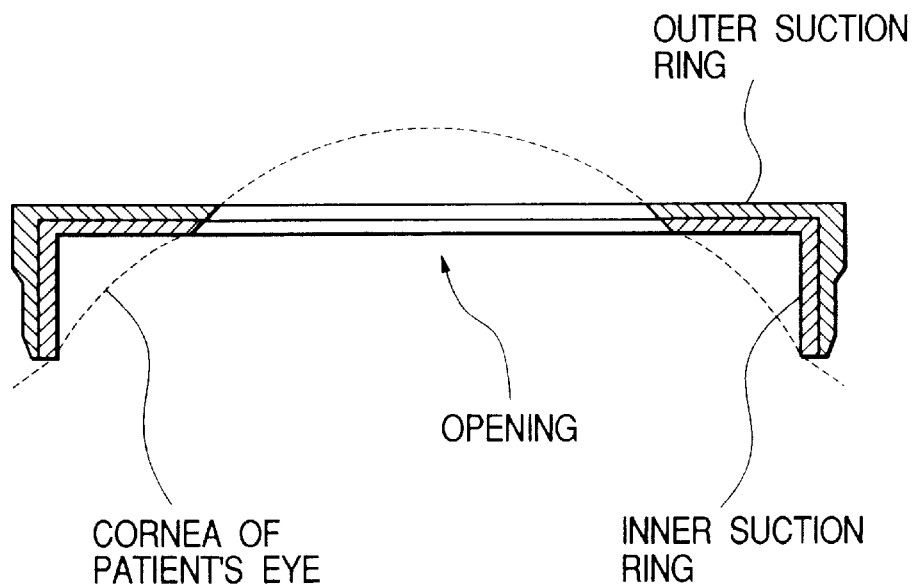
FIG. 11a) and FIG. 11(b) are explanatory diagrams illustrating a height-adjustable suction ring.
Figure 11B:
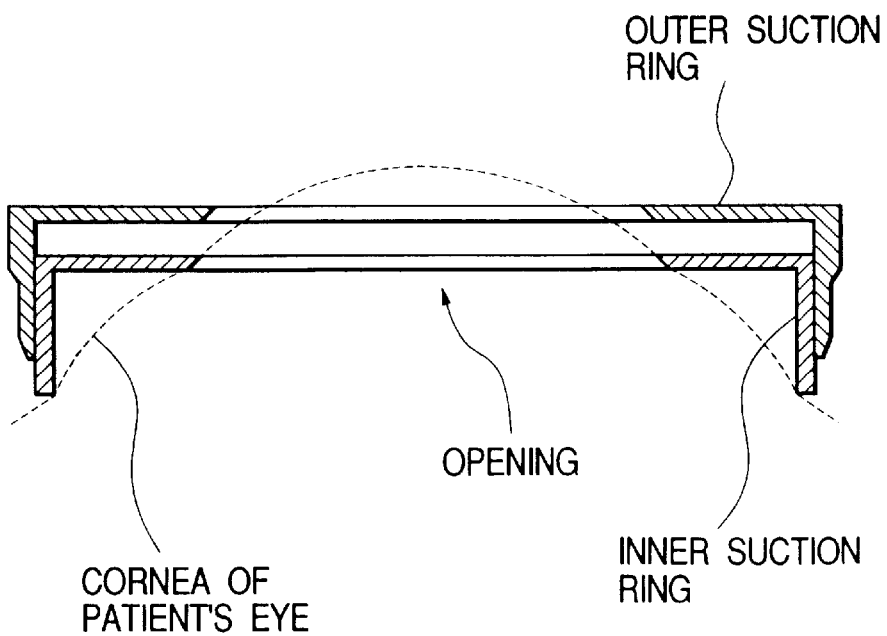

The feed motor 11, the oscillating motor 12, the feed screw 13, the attaching member 14, and the connecting member 17 are vertically (in the Y direction) movable inside the main body 1 (these members are immovable in the Z direction). Reference numeral 60 denotes a height adjusting dial, reference numeral 61a denotes a gear attached to a rotating shaft of the dial 60, reference numeral 61b denotes a rack attached to the motor 11 and meshing with the gear 61a, reference numeral 61c denotes a plunger provided fixedly in the main body 1, and reference numeral 61d denotes a guide rail for guiding an unillustrated guide member fixed to the motor 11. By virtue of this arrangement, as the dial 60 is rotated, the motor 11, the motor 12, the screw 13, the attaching member 14, and the connecting member 17 are integrally moved vertically in parallel along the guide rail, so that the height position of the cutting unit 2 attached to the connecting member 17 can be varied. In addition, a ball of the plunger 61c is fitted in a receiving groove provided in the dial 60, so that the vertical position of the motor 11 and the like is fixed. Reference numeral 62 denotes a spring-loaded shield member. FIG. 10B is a diagram for explaining the shield member 62. A left part and a central part of FIG. 10B shows the shield member 62 used in this embodiment. The shield member 62 includes a rubber-made shield 62a fixed to the connecting member 17, and a spring 62b interposed between and fixed to the shield 62 and the inner wall of the main body 1. A right part of FIG. 10B shows the shield member 62' adapted to the connecting member 17 rectangular in outer configuration. FIG. 10C shows a modification of the shield member which is made up of a rubber-made shield 72 but does not employ the spring 62b.

Figure 8:
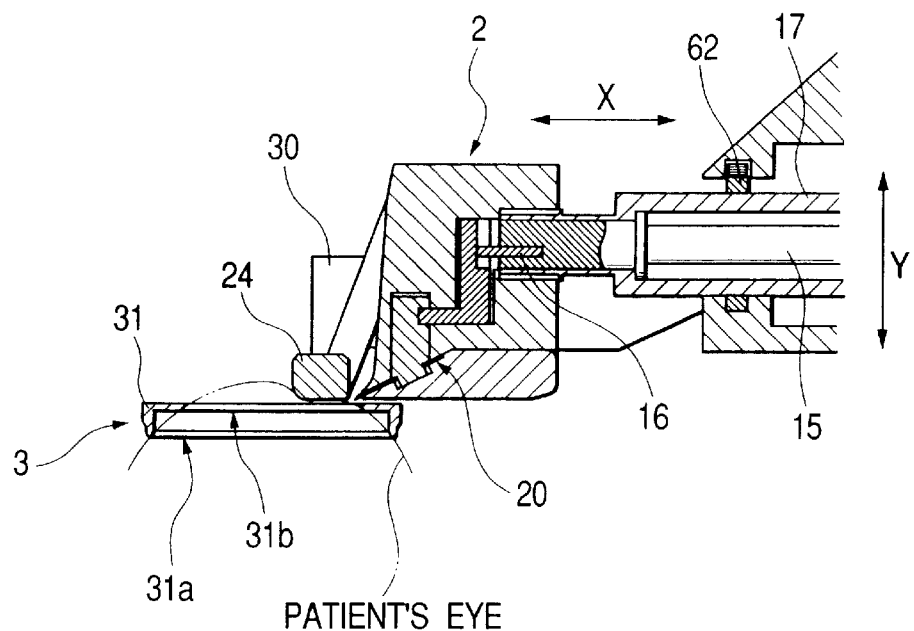
FIG. 8 is an explanatory diagram illustrating how the height of a blade relative to a suction ring is changed in the second embodiment.

In the same way as the first embodiment, upon completion of the fixing of the apparatus through suction and fixation by the suction ring 31, the cutting unit 2 is moved vertically by rotating the dial 60 to adjust the height of the tip (blade edge) of the blade 20 with respect to the suction ring 31 (see FIG. 8). If the cutting unit 2 is moved upward, the height of the blade edge becomes large, and a small flap is formed as compared to a original or neutral state of the cutting unit 2. On the other hand, if the cutting unit 2 is moved downward, the height of the blade edge becomes small, and a large flap is formed as compared to the original or neutral state of the cutting unit 2. Accordingly, it suffices that in a case where the corneal curvature is large and the height of the cornea projecting from the suction ring 31 becomes large, the cutting unit 2 is moved upward, whereas in a case where the corneal curvature is small and the height of the cornea projecting from the suction ring 31 becomes small, the cutting unit 2 is moved downward. Similarly, it suffices that in a case where the flap diameter is to be small, the cutting unit 2 is moved upward, whereas if the flap diameter is to be large, the cutting unit 2 is moved downward.

Figure 9:
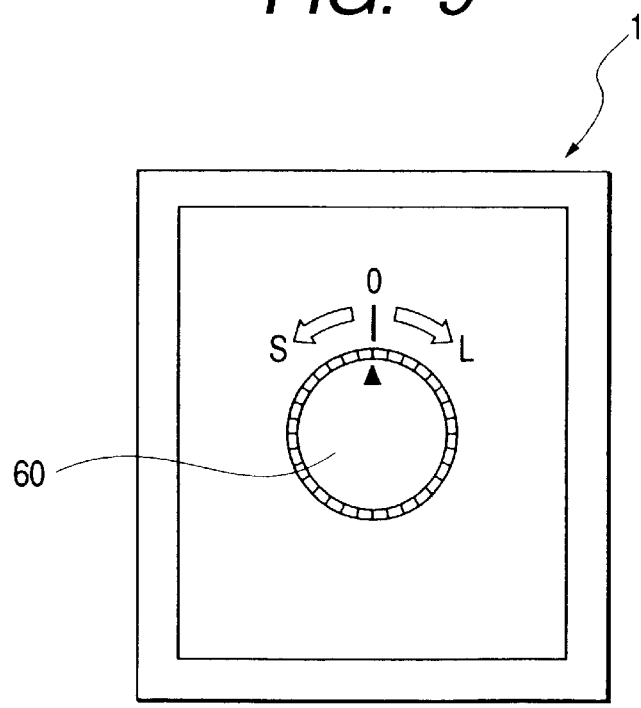
FIG. 9 is an explanatory diagram illustrating how the height of the blade relative to the suction ring is notified to an operator in the second embodiment.

It should be noted that the state of movement of the cutting unit 2 (i.e. the height of the blade edge) can be known from the amount of rotation of the dial 60 (see FIG. 9). When the dial 60 is rotated clockwise, the cutting unit 2 is moved downward, so that the flap is formed to be large. Meanwhile, when the dial 60 is moved counterclockwise, the cutting unit 2 is moved upward, so that the flap is formed to be small. Further, if graduations for positions of movement which impart optimum flap diameters depending on the values of the corneal curvature are inscribed in advance, the use of the apparatus can be facilitated.

Incidentally, it goes without saying that, as the method for adjusting the height of the tip of the blade 20, known techniques may be used other than the above-described methods.

As described above, in accordance with the invention, it is possible to form a flap of an uniform diameter with a simple arrangement irrespective of the difference in the corneal curvature. In addition, the flap diameter can be varied simply.

What is claimed is:

1. A corneal surgical apparatus for incising a cornea of a patient's eye in a layered form, comprising:
    a suction ring having an opening, which is vacuum-fixed to the patient's eye so that the cornea is projected from the opening;
    incising means, having a blade and an applanating member, for incising the cornea projected from the opening using the blade while applanating the cornea using the applanating member; and
    height changing means for changing a height of a tip of the blade in a visual axis direction of the patient's eye with respect to the suction ring.

2. The apparatus of claim 1, wherein the incising means includes a shaft for linearly moving the blade in an incise direction, and the height changing means includes tilting means for tilting the shaft in the visual axis direction.

3. The apparatus of claim 2, wherein the tilting means includes a fulcrum member about which the shaft is inclined.

4. The apparatus of claim 1, wherein the incising means includes a shaft for linearly moving the blade in an incise direction, and the height changing means includes moving means for translating the shaft parallelly in the visual axis direction.

5. The apparatus of claim 4, wherein the moving means includes a guide member for guiding parallel translation of the shaft.

6. The apparatus of claim 1, wherein the incise means includes a shaft for linearly moving the blade in an incise direction, first driving means for moving the shaft forwardly, second driving means for rotating the shaft, and transmitting means for converting rotation of the shaft into lateral oscillations and transmitting the lateral oscillations to the blade.

7. The apparatus of claim 1, further comprising:
    informing means for providing information concerning the height of the tip of the blade in the visual axis direction, changed by the height changing means.

8. A corneal surgical apparatus comprising:

a main body;

a suction ring fixedly provided on the main body, the suction ring having an opening;

a cutting unit movable substantially along a plane of the opening;

a drive unit supporting the cutting unit;

a support movably supporting the drive unit to the main body, and holding, through the drive unit, the cutting unit at a variable position in a direction substantially perpendicular to the plane of the opening.

9. The apparatus of claim 8, wherein the support includes a fulcrum member about which the drive unit is pivotable, and a threading member rotatably held by the main body and threadingly engaged with the drive unit.

10. The apparatus of claim 8, wherein the support includes a guide rail movably supporting the drive unit, a rack member provided to the drive unit, and a pinion member rotatably held by the main body and meshed with the rack member.

* * * * *